(12) United States Patent
Knopff

(10) Patent No.: US 8,173,846 B2
(45) Date of Patent: May 8, 2012

(54) SUBSTITUTED CYCLOHEXENONES

(75) Inventor: Oliver Knopff, Geneva (CH)

(73) Assignee: Firmenich SA, Geneva (CH)

( * ) Notice: Subject to any disclaimer, the term of this patent is extended or adjusted under 35 U.S.C. 154(b) by 173 days.

(21) Appl. No.: 12/810,735

(22) PCT Filed: Jan. 8, 2009

(86) PCT No.: PCT/IB2009/050070
§ 371 (c)(1),
(2), (4) Date: Jun. 25, 2010

(87) PCT Pub. No.: WO2009/095804
PCT Pub. Date: Aug. 6, 2009

(65) Prior Publication Data
US 2010/0274059 A1    Oct. 28, 2010

(30) Foreign Application Priority Data

Feb. 1, 2008 (WO) .................. PCT/IB2008/050389

(51) Int. Cl.
*C07C 45/61* (2006.01)
(52) U.S. Cl. ...................................................... 568/343
(58) Field of Classification Search ............. 568/343
See application file for complete search history.

(56) References Cited

U.S. PATENT DOCUMENTS

| | | | |
|---|---|---|---|
| 2006/0252967 A1 | 11/2006 | Knopff | 586/341 |
| 2008/0228008 A1 | 9/2008 | Knopff et al. | 586/376 |

FOREIGN PATENT DOCUMENTS

| | | |
|---|---|---|
| WO | WO 2005/077875 A1 | 8/2005 |
| WO | WO 2007/010483 A1 | 1/2007 |

OTHER PUBLICATIONS

International Search Report and Written Opinion of the International Searching Authority, application No. PCT/IB2009/050070, mailed Mar. 4, 2009.

Agami et al., "Enantioselective cyclizations of acyclic 1,5-diketones," Bulletin de la Société Chimique de France, 2:358-360 (1987).

Nagamine et al., "Amino Acid Mediated Intramolecular Asymmetric Aldol Reaction to Construct a New Chiral Bicyclic Enedione Containing a Seven-Membered Ring: Remarkable Inversion of Enantioselectivity Compared to the Six Membered Ring Example," J. Org. Chem., 72:123-131 (2007).

*Primary Examiner* — Sikarl Witherspoon
(74) *Attorney, Agent, or Firm* — Winston & Strawn LLP

(57) ABSTRACT

The present invention relates to a method of preparation of an optically active cyclohexenone derivative of Formula (I) OR1R2*R1 and wherein $R^1$ and $R^2$ are organic residues.

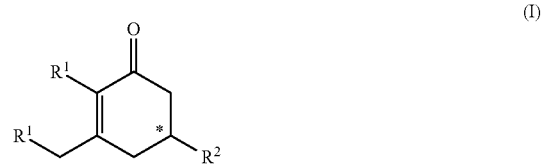

15 Claims, No Drawings

SUBSTITUTED CYCLOHEXENONES

This application is a 371 filing of International Patent Application PCT/IB2009/050070, filed Jan. 8, 2009.

TECHNICAL FIELD

The present invention relates to the field of organic synthesis and more specifically it concerns a method of preparation of an optically active cyclohexenone derivative of formula

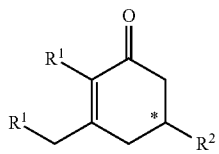

(I)

wherein $R^1$ and $R^2$ are as defined below.

PRIOR ART

Optically active cyclohexenone derivatives are useful intermediates or building-blocks for the synthesis of various more complex compounds, such as steroids or macrocyclic ketones, which are known to be useful musk odorants like some $C_{14}$, $C_{15}$ or $C_{16}$ 3-methyl cycloalkenones.

Despite this fact, to the best of our knowledge, the prior art reports only few processes to prepare an optically active cyclohexenone derivative from an achiral diketone or aldol adduct.

In the patent applications WO 2005/077875 and WO 2007010483, there is described the use of chiral amino alcohol salts and the use as starting material of either an achiral di-ketone or an achiral aldol adduct.

In another document (see C. Agami et al. in Bulletin de la Societe Chimique de France, 1987, 358), it is reported the use of a catalytic amount of L-proline (a secondary amino acid) to obtain a cyclohexenone similar to the one of present invention. However, as will be shown further below, in the Example said method is ineffective when applied to the substrate of the present invention.

It is therefore an aim of the present invention to provide an alternative, and effective, method to prepare heavier optical active cyclohexenones of formula (I).

DESCRIPTION OF THE INVENTION

We have now found that an optically active compound (I) can be prepared in catalytic manner using some amino acids derivatives to promote the reaction.

Therefore a first object of the present invention is a process for the preparation of a compound of formula

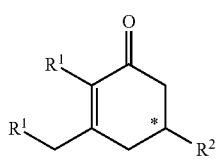

(I)

wherein the asterisk means that said compound (I) is in an optically active form;

the $R^1$, taken separately, are identical and represent an achiral $C_{1-7}$ linear, branched or cyclic alkyl, alkenyl or alkynyl group optionally substituted, or alternatively said two $R^1$, taken together, represent a linear $C_2$-$C_{12}$ alkanediyl, alkenediyl or alkyndiyl group optionally substituted;

$R^2$ represents an achiral $C_{1-7}$ linear, branched or cyclic alkyl or alkenyl group optionally substituted or a phenyl or benzyl group optionally substituted;

by treating a ketone of one of formulae

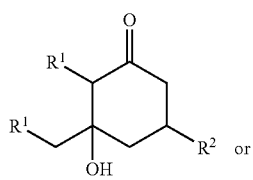

(II)

or

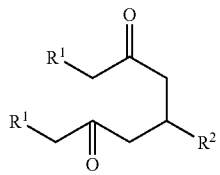

(III)

wherein the asterisk, $R^1$ and $R^2$ have the meaning indicated above and compound (II) can be in the form of any one of its stereoisomers, diasteroisomers or of a mixture thereof;

with a reacting system comprising at least one salt of an optically active primary amino acid, or at least one optically active primary amino acid, or a mixture thereof.

According to a particular embodiment of the invention, the two $R^1$ are taken together and represent a linear $C_6$-$C_{12}$ alkanediyl or alkenediyl group optionally substituted.

According to a particular embodiment of the invention, $R^2$ represents an achiral $C_{1-3}$ linear or branched, or a $C_{5-6}$ cyclic, alkyl or alkenyl group or a phenyl or benzyl group. More particularly, said $R^2$ may represent a methyl or phenyl group.

As mentioned above, $R^1$ and $R^2$ can be substituted, for example by one or two groups. As non-limiting examples, said groups are $C_{1-5}$ alkyl, alkoxy or cycloalkyl group.

It is understood that according to the above embodiments, the corresponding ketones (II) or (III) are those having the same meaning for $R^1$ and $R^2$.

However, in the case where a ketone (II) is used as starting material, according to a further embodiment of the invention, said compound is of formulae (II') or (II")

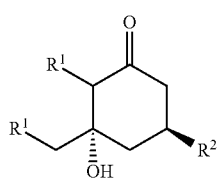

(II')

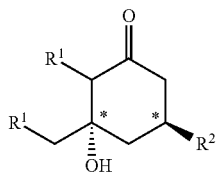

(II'')

wherein the OH and R² substituents are in a trans relative configuration and the asterisk means that said compound (II'') is in an optically active form.

Examples of specific embodiments of said compound (I) is (S)-14-methylbicyclo[9.4.0]-pentadec-1(11)-en-12-one or (R)-14-methyl-bicyclo[9.4.0]-pentadec-1(11)-en-12-one or an optically active mixture of said stereoisomers and the starting ketone is 3-methyl-1,5-cyclopentadecanedione. In another embodiment, said compound (I) is 15-methylbicyclo[10.4.0]hexadec-1(12)-en-13-one and the starting ketone is 3-methyl-1,5-cyclohexadecanedione.

The invention's process is also useful for the preparation of the optically active 13-methylbicyclo[8.4.0]tetradec-1(10)-en-11-one or 15-methylbicyclo[10.4.0]hexadec-1(12)-en-13-one which are intermediates for the preparation of the known musk ingredients 3-methyl-5-cyclotetradecene-1-one or 3-methyl-5-cyclohexadecen-1-one respectively.

The reacting system required to carry out the invention's process comprises, as anticipated above, either an optically active primary amino acid in the form of salt or an optically active primary amino acid, or a mixture thereof.

By "optically active primary amino acid" we mean here an α-amino acid wherein the amino group is a NH₂ group, and wherein said amino acid possesses an enantiomeric excess (e.e.) comprised between 100% and 5%.

In general, optically active primary amino acids or salts having a higher e.e. provided compounds (I) with higher e.e. Therefore, according to a particular embodiment of the invention, in said invention's process there is used an optically active primary amino acid having e.e. of at least 50% or even of at least 90%.

Said salt of an optically active primary amino acid can be in the form of a carboxylate salt or of an ammonium salt. In particular said salt can be a compound of formula

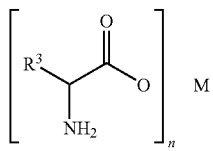

(III)

wherein R³ represents C₆-C₁₁ hydrocarbon group comprising 3 to 7 nitrogen and/or oxygen atoms or a C₁-C₁₆ hydrocarbon group optionally comprising from one to four heteroatoms such as oxygen, nitrogen, sulfur, phosphorous, halogen and/or selen; and M represents
- an alkaline cation or a C₄-C₁₅ quaternary ammonium, and n is 1;
- an alkaline-earth cation, and n is 2; or
- a lanthanide or a Group (III) (i.e. Y, Sc, La) cation, and n is 3.

In particular, said group R³ can be the residue of a nature occurring amino acid or of a derivative thereof, in other words, said salt is derived from a natural amino acid.

According to a particular embodiment of the invention, R³ may represent a C₁-C₁₀ hydrocarbon group optionally comprising one, two or three oxygen, nitrogen and/or sulfur atoms.

According to a particular embodiment of the invention, R³ may represent one of the following groups:
- a group of formula (C₆H₃(NO₂)₂)NH(CH₂)₄;
- a linear, branched or cyclic C₁-C₇ alkyl or alkenyl group;
- a (CH₂)₍c₎R⁴ group wherein c is 1 or 2, and R⁴ represents a COOR⁵ or CON(R⁵)₂, R⁵ representing a hydrogen atom or a benzyl group or a C₁-C₅ alkyl or an allyl group;
- a CH₂R⁶ group, R⁶ representing a C₃-C₉ heterocycle comprising three heteroatoms such as oxygen, nitrogen and/or sulfur;
- a CH₂OR⁵ or CH(OR⁵)CH₃ group, R⁵ having the meaning provided above;
- a CH₂(CH₂)₍c₎R⁷, R⁷ being a NHC(NH)NH₂, a CH₂N(R⁵)₂, a N(R⁵)₂ or a CH(NH₂)COOR⁵ group, c and R⁵ having the meaning provided above;
- a (CH₂)₍c₎C₆H₅₋ᵥR⁵'ᵥ group, wherein R⁵' represents a R⁵ group, a nitro group, a NR⁵₂ group or a OR⁵ group or an halide, v is 0, 1 or 2, and c and R⁵ having the meaning provided above; or
- a (CH₂)₍c₎S(O)₍a₎(Q)₍b₎R⁸ group, wherein a and b represent 0 or 1, Q being O or NH, R⁸ represents a hydrogen atom, a R⁵ group, a trytyl group or a (CH₂)₍d₎(C₆H₅₋ᵥR⁵'ᵥ) group, d being 0 or 1, and wherein v, c and R⁵' having the meaning provided above.

According to a particular embodiment of the invention, said R³ group represents:
- a linear, branched or cyclic C₃-C₇ alkyl group, such as isopropyl, isobutyl, sec-butyl or cyclohexylmethyl;
- a (CH₂)₍c₎R⁴ group wherein c is 1 or 2, and R⁴ represents a COOH or CONH₂;
- a CH₂R⁶ group, R⁶ an C₃H₃N₂ or a C₈H₆N heterocyclic group;
- a CH₂(CH₂)₍c₎R⁷, R⁷ being a NHC(NH)NH₂, a CH₂NH₂ group, c having the meaning provided above;
- a (CH₂)₍c₎C₆H₅₋ᵥR⁵'ᵥ group, wherein R⁵' represents a R⁵ group, nitro group or a OR⁵ group, v is 0, 1 or 2, R⁵ representing a hydrogen atom or a methyl or benzyl group, and c having the meaning provided above;
- a (CH₂)₂S(O)₂R⁹ or a (CH₂)₂S(O)(NH)R⁹, wherein R⁹ represents a C₁-C₅ alkyl group; or
- a (CH₂)₍c₎SR⁸ group, wherein R⁸ represents a hydrogen atom, a methyl group, or a CH₂(C₆H₅₋ᵥR⁵'ᵥ) group, wherein v, c and R⁵' having the meaning provided above.

According to a particular embodiment of the invention, M is an alkaline cation, Ba²⁺, a C₆-C₁₀ quaternary ammonium, La³⁺.

According to another embodiment, said M can be advantageously chosen amongst Li⁺, Na⁺, K⁺, Rb⁺, Cs⁺, Ba²⁺, La³⁺ or (C₆H₅CH₂)(Me)₃N⁺.

Alternatively, said salt can be a compound of formula

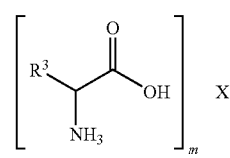

(IV)

wherein $R^3$ has the same meaning as in formula (III) and X represents nitrate, hydrogeno sulfate, hydrogeno carbonate, an halide, a $C_0$-$C_{18}$ sulfonate, $C_0$-$C_{24}$ borate, a $C_2$-$C_{18}$ phosphonate or phosphate or phosphinate, or a $C_1$-$C_{12}$ mono carboxylate, and m is 1; or sulfate, carbonate or a $C_2$-$C_{12}$ di-carboxylate, and m is 2, or an anion of formula $H_vPO_3^{(3-v)-}$, v being 0, 1 or 2, and m is 1, 2 or 3.

According to a particular embodiment of the invention, X is $Cl^-$, $C_0$-$C_7$ sulfonate, $BF_4^-$, $B(C_6H_5)_4^-$, $(R^4O)_2P(O)O^-$, $R^4{}_2P(O)O^-$ or $R^4P(O)(OH)O^-$, wherein $R^4$ represents a $C_1$-$C_7$ hydrocarbon group, a $C_1$-$C_6$ mono carboxylate, a $C_2$-$C_6$ di-carboxylate or $HPO_3^{2-}$.

According to another embodiment, said X can be advantageously chosen amongst $CF_3SO_3^-$, $nC_{18}H_{30}SO_3^-$, $HSO_4^-$, $CH_3CO_2^-$, $ClCH_2CO_2^-$, camphor sulfonate, $C_6H_5SO_3^-$, $MeC_6H_5SO_3^-$, $BF_4^-$, $(C_6H_5O)_2P(O)O^-$, $(BuO)_2P(O)O^-$, $(C_6H_5)_2P(O)O^-$, $(tBu)P(OH)_2O^-$, $(C_6H_5)P(OH)_2O^-$, a $C_1$-$C_3$ alkyl carboxylate, $CF_3COO^-$, $(CF_3SO_3)_2N^-$, oxalate or phthalate.

The amino acid salt can be used in the form of a preformed salt or it can be formed in situ prior to its use, e.g. by pre-mixing a primary amino acid and an appropriate salt of cation M or anion X, such as a basic salt of M or an acidic salt of X. Typical examples of said salt of cation M or X are provided in the Example herein below.

The reacting system may also comprise an optical active primary amino acid, i.e. a compound of formula $R^3CH(NH_2)COOH$, wherein $R^3$ has, preferably, the same meaning as above.

As mentioned above, the salts of formula (III) or (IV) can be obtained from a compound of formula $R^3CH(NH_2)COOH$. As non limiting examples of said optical active primary amino acid, used to generate the salts of formula (III) or (IV) or as components of the reacting system, one may cite, as non-limiting examples the following: phenylalanine, cysteine and its S-substituted derivatives—such as phenylcysteine, benzylcysteine or tritylcysteine—tyrosine and its O-substituted derivatives—such as O-methyl tyrosine or O-benzyl tyrosine—dimethoxyphenylalanine, p-$NO_2$-phenylalanine, tryptophane, valine, methionine, methionine sulfone/sulfoxide or yet buthionine sulfoximine, asparagines or lysine; said amino acid being in an optically active form.

According to a particular embodiment of the invention, the reacting system comprises:

at least one salt of an optically active primary amino acid; and optionally at least one optically active primary amino acid.

According to a particular embodiment of the invention, when a salt of an optically active primary amino acid is used together with an optically active primary amino acid, then said acids are the same, e.g. the $R^3$ groups are identical for both compounds.

According to a particular embodiment of the invention, only one type of amino acid salt is used and optionally only one type of amino acid.

According to a particular embodiment of the invention's process, an amino acid salt of formula (III) is used.

The salt of an optically active primary amino acid (amino acid salt) or the optically active primary amino acid (amino acid) can be added to the reaction medium in a large range of concentrations, relative to the starting material (II) or (III). Said amounts can be stoechiometric ones, or above stoechiometry or even in catalytic amounts, i.e. sub-stoechiometric amounts.

As non-limiting examples, one can cite as amino acid salt total amount values ranging from 0 to 3 molar equivalents, relative to the starting ketone (II) or (III). Preferably, the optically active primary amino acid salt total concentration will be comprised between 0.05 and 1.5 molar equivalents. Even more precisely, according to some embodiments of the invention, the amino acid salt total concentration will be comprised between 0.1 and 1.0 molar equivalents. It goes without saying that the optimum concentration of said amino acid salt will depend on the nature of the latter and on the desired time of reaction.

Similarly, as non-limiting examples, one can cite as amino acid total concentration values ranging from 0.0 to 3 molar equivalents, relative to the starting ketone (II) or (III). Preferably, the optically active primary amino acid total concentration will be comprised between 0.05 and 1.0 molar equivalents.

Even more precisely, according to some embodiments of the invention, the amino acid total concentration will be comprised between 0.1 and 10 molar equivalents relative to the amino acid salt total concentration.

Again, it goes without saying that the optimum concentration of said amino acid will depend on the nature of the latter and on the desired time of reaction.

A by-product of the invention's process is water. According to a particular embodiment of the invention, the process can be performed in the presence of a means of removing water. According to a preferred embodiment of the invention, the process is carried out in the presence of said water-removing means.

By "a means of removing water" we mean here a compound or a substance capable of trapping the water which is formed during the reaction (chemical means), or any experimental conditions capable of removing water from a reaction medium (physical means). In other words, said means can remove from the reaction medium the water formed during the reaction either by a chemical mechanism (e.g. absorption mechanism or by means of a chemical reaction) or by a physical mechanism (e.g. normal distillation or azeotropic distillation).

Typical, non-limiting examples of useful chemical means are:

i) an alkaline or alkaline earth hydride, such as NaH, KH, $CaH_2$, LiH, $MgH_2$;

ii) a reaction-medium insoluble inorganic material capable to form a clathrate with water, such as an anhydrous zeolite, preferably of the 4 or 5 Å type, or anhydrous $MgSO_4$, $Na_2SO_4$, $Na_2O$, $CaCl_2$ or $MgCl_2$; or iii) an organic material capable of reacting with water to form non-acidic compounds, such as an orthoester, N-methyl-N-trimethylsilyl-trifluoroacetamide or 1-trimethyl-silylimidazole.

The chemical water-removing means can be added to the reaction medium in a large range of amounts which depend on the exact nature of the water-removing means. In general, it has been observed that the higher the amount of means of removing water employed, or the more effective, the better it is for the process. However, the addition of amounts which exceed three times the amount theoretically needed to trap all the water which can theoretically be formed does not provide any appreciable additional benefit. The same reasoning applies also when there is used a physical means to remove water.

The invention's process can be carried out in the presence of a solvent. Said solvent must be chemically compatible with the reaction and does not deactivate the catalytic system.

A suitable solvent is one which is an organic protic or aprotic solvent which possesses a boiling point compatible with the experimental conditions. Non-limiting examples of such a solvent are $C_3$-$C_9$ ethers, esters, amides, aromatic hydrocarbons, linear or branched or cyclic hydrocarbons, chlorinated solvents and mixtures thereof. More preferably, the solvent is a $C_4$-$C_6$ ether such as THF, 2-methyl-THF, or dioxane, $C_3$-$C_6$ amides such as DMF or N-Methyl pyrrolidone, methylene chloride, toluene, p-xylene, N-methyl morpholine, tetronic, sulfolane, DMSO, tetraglyme and mixtures thereof.

The temperature, at which this process of the invention can be carried out, in any of its embodiments, is comprised between 10° C. and 150° C., preferably between 20° C. and 100° C. Of course a person skilled in the art is also able to select the preferred temperature as a function of the melting and boiling point of the starting and final products and/or an eventual solvent.

EXAMPLES

The invention, in all its embodiments, will now be described in further detail by way of the following examples, wherein the abbreviations have the usual meaning in the art, the temperatures are indicated in degrees centigrade (° C.); the NMR spectral data were recorded in $CDCl_3$ with a 360 MHz or 100 MHz machine for $^1H$ or $^{13}C$ respectively, the chemical displacements δ are indicated in ppm with respect to TMS as standard, the coupling constants J are expressed in Hz.

Example 1

Preparation of Optically Active 14-methyl-bicyclo[9.4.0]-pentadec-1(11)-en-12-one a) General Procedure:

In the reaction vessel, the catalytic system was formed in situ by stirring the optically active primary amino acid with an appropriate salt of the cation M or anion X, at 60-70° C. in 0.5 ml DMSO under vacuum (8 mbar) for 18 hours. Then 250 mg of 3-methyl-1,5-cyclopentadecanedione were introduced in 0.7 ml of DMSO. The total amount of DMSO present was calculated in order to keep the concentration of the starting diketone between 0.1 and 1 M at the beginning of the reaction.

The reaction mixture was stirred under vacuum (8 mbar) at 60° C. and followed by GC. To to stop the reaction, the mixture was hydrolyzed with water or an aqueous saturated $NH_4Cl$ solution. After extraction of the aqueous layer with diethyl ether, the organic layer was dried over $MgSO_4$ and filtered. The solvent was removed under vacuum and the residue was purified either by flash chromatography or by bulb to bulb distillation to yield in the desired product, i.e. (S)-14-methyl-bicyclo[9.4.0]-pentadec-1(11)-en-12-one or (R)-14-methyl-bicyclo[9.4.0]-pentadec-1(11)-en-12-one or an optically active mixture of said stereoisomers depending on the configuration of the amino acid.

$^1$H-NMR: 1.04 (d, J=6.1, 3H), 1.18-1.46 (m, 10H), 1.50-1.75 (m, 4H), 1.97-2.15 (m, 3H), 2.30-2.40 (m, 3H), 2.41-2.56 (m, 3H).
$^{13}$C-NMR: 21.3, 23.5, 24.6, 25.1, 25.3, 25.5, 26.0, 26.2, 26.6, 29.7, 32.3, 38.3, 46.7, 136.3, 158.2, 199.7.

The results obtained are shown in Table 1.

TABLE 1 yields and e.e. of the final product as a function of the catalytic system used

| | | Catalytic system[a] | | | | |
|---|---|---|---|---|---|---|
| Amino acid[b] | Eq.[1] | Salt of the cation M or anion X | Eq.[1] | t[2] | Yield[3] | e.e[4] |
| D-Met | 0.5 | CsOH•$H_2O$ | 0.3 | 1 | 80% | 57% ee (S) |
| D-Met* | 0.5 | CsOH•$H_2O$ | 0.3 | 1 | 79% | 56% ee (S) |
| D-Met | 0.5 | CsOH•$H_2O$ | 0.1 | 2 | 78% | 56% ee (S) |
| D-Met[6] | 0.5 | CsOH•$H_2O$ | 0.3 | 1 | 77% | 57% ee (S) |
| D-Met[5,7] | 1 | CsOH•$H_2O$ | 0.3 | 1 | 30% | 54% ee (S) |
| L-Met sulfone | 0.5 | CsOH•$H_2O$ | 0.3 | 3 | 80% | 53% ee (R) |
| D-Met | 0.5 | RbOH (50% $H_2O$) | 0.3 | 1 | 90% | 56% ee (S) |
| D-Met* | 0.5 | RbOH (50% $H_2O$) | 0.3 | 1 | 84% | 50% ee (S) |
| D-Met[5] | 1 | KOH | 0.3 | 2 | 83% | 47% ee (S) |
| D-Met[5] | 1 | KOH | 0.3 | 5 | 99% | 47% ee (S) |
| D-Met* | 0.5 | KOH | 0.3 | 1 | 66% | 54% ee (S) |
| D-Met | 0.5 | NaOH | 0.3 | 1 | 88% | 54% ee (S) |
| D-Met | 0.5 | LiOH | 0.3 | 3 | 92% | 51% ee (S) |
| D-Met* | 0.5 | $Cs_2CO_3$ | 0.15 | 3 | 88% | 52% ee (S) |
| D-Met* | 0.5 | CsF | 0.3 | 3 | 97% | 49% ee (S) |
| D-Met | 0.5 | La(OH)$_3$ | 0.3 | 3 | 57% | 47% ee (S) |

TABLE 1-continued yields and e.e. of the final product as a function of the catalytic system used

| Amino acid[b] | Eq.[1] | Salt of the cation M or anion X | Eq.[1] | t[2] | Yield[3] | e.e[4] |
|---|---|---|---|---|---|---|
| D-Met | 0.5 | BnN(CH$_3$)$_3$OH (40% H$_2$O) | 0.3 | 3 | 59% | 48% ee (S) |
| D-Met | 0.5 | KCl | 0.3 | 3 | 59% | 43% ee (S) |
| D-Met | 0.5 | Ba(OH)$_2$ | 0.25 | 2 | 76% | 40% ee (S) |
| D-Met | 0.5 | NaCl | 0.3 | 3 | 63% | 46% ee (S) |
| D-Phe* | 1 | Oxalic acid | 0.5 | 7 | 51% | 49% ee (S) |
| D-Met* | 0.5 | KH | 0.3 | 1 | 83% | 58% ee (S) |
| D-Met* | 0.5 | NaH | 0.5 | 5 | 82% | 48% ee (S) |
| L-Trp | 0.5 | CsOH•H$_2$O | 0.3 | 1 | 99% | 34% ee (R) |
| O—Me-L-Tyr | 0.5 | CsOH•H$_2$O | 0.3 | 6 | 72% | 48% ee (R) |
| L-Tyr | 0.5 | CsOH•H$_2$O | 0.3 | 2 | 99% | 30% ee (R) |
| L-Leu | 0.5 | CsOH•H$_2$O | 0.3 | 1 | 30% | 45% ee (R) |
| L-Val | 0.5 | CsOH•H$_2$O | 0.3 | 3 | 82% | 52% ee (R) |
| L-Lys | 0.5 | CsOH•H$_2$O | 0.3 | 2 | 93% | 52% ee (R) |
| L-Asn | 0.5 | CsOH•H$_2$O | 0.3 | 2 | 27% | 50% ee (R) |
| L-BnCys[5),8)] | 1 | CsF | 0.3 | 1 | 41% | 41% ee (R) |
| L-Trp[5),8)] | 1 | CsF | 0.3 | 1 | 72% | 35% ee (R) |
| L-Pro[9)] | 0.2 | — | — | 5 | 0% | — |
| L-Pro[10)] | 0.5 | CsOH•H$_2$O | 0.3 | 1 | 1% | — |
| Se-L-Meth | 0.5 | CsOH•H$_2$O | 0.3 | 1 | 92% | 56% ee (R) |
| Iso-L-Leu | 0.5 | CsOH•H$_2$O | 0.3 | 2 | 69% | 35% ee (R) |
| L-Ala | 0.5 | CsOH•H$_2$O | 0.3 | 2 | 68% | 43% ee (R) |
| L-HomoSer | 0.5 | CsOH•H$_2$O | 0.3 | 2 | 68% | 52% ee (R) |
| S-Prop-L-Cys | 0.5 | CsOH•H$_2$O | 0.3 | 2 | 20% | 61% ee (R) |
| Dimethoxy-L-Phe | 0.5 | CsOH•H$_2$O | 0.3 | 2 | 38% | 57% ee (R) |
| D-Homo-Phe | 0.5 | CsOH•H$_2$O | 0.3 | 2 | 69% | 43% ee (S) |
| p-Nitro-L-Phe | 0.5 | CsOH•H$_2$O | 0.3 | 1 | 22% | 48% ee (R) |
| L-But-sulfox | 0.5 | CsOH•H$_2$O | 0.3 | 2 | 90% | 51% ee (R) |
| 1-meth-D-Trp | 0.5 | CsOH•H$_2$O | 0.3 | 2 | 91% | 41% ee (S) |
| D-Met* | 0.5 | KOH | 0.5 | 1 | 54% | 47% ee (S) |
| D-Met* | 0.5 | CsOH•H$_2$O | 0.1 | 1 | 77% | 63% ee (S) |
| D-Met | 0.5 | NaOH | 0.3 | 1 | 63% | 59% ee (S) |
| D-Pyr-Ala | 0.5 | CsOH•H$_2$O | 0.3 | 1 | 100% | 54% ee (S) |
| L-Nor-Val | 0.5 | CsOH•H$_2$O | 0.3 | 1 | 60% | 46% ee (S) |
| 4-F-D-Phe | 0.5 | CsOH•H$_2$O | 0.3 | 1 | 65% | 50% ee (R) |
| L-Homo-Phe | 0.5 | CsOH•H$_2$O | 0.3 | 1 | 58% | 36% ee (R) |
| N-ε-acetyl-L-Lys | 0.5 | CsOH•H$_2$O | 0.3 | 2 | 88% | 40% ee (R) |
| o-bz-L-Ser | 0.5 | CsOH•H$_2$O | 0.3 | 2 | 72% | 38% ee (R) |
| α-amicycloh-prop-acid | 0.5 | CsOH•H$_2$O | 0.3 | 2 | 81% | 38% ee (S) |
| S-Eth-L-Cys | 1 | CsOH•H$_2$O | 0.5 | 2 | 98% | 51% ee (R) |
| L-Trp | 0.5 | — | — | 3 | 100% | 34% ee (R) |
| D-Met | 0.5 | CsOH•H$_2$O | 0.1 | 2 | 94% | 60% ee (R) |

*the amino acid, the salt of the cation M or anion X and the starting diketone were reacted directly under vacuum in DMSO at 60° C.
[a)] The catalytic system comprises a mixture of the optically active primary amino acid in the form of a salt and of the optically active primary amino acid
[b)] Optically active primary amino acid
[1)] Number of molar equivalents introduced, relative to the starting diketone
[2)] Duration of the reaction in days
[3)] Determined by GC
[4)] Determined by reacting the final product with an excess of LiAlH$_4$ in dry THF. After hydrolysis, filtration and extraction in Et$_2$O, the allyl alcohol obtained was analyzed by GC with a chiral column (CHIRASIL DEX DB) to determine the enantiomeric excess of the resulting allyl alcohol
[5)] The reaction was performed in 2.4 ml DMSO
[6)] The reaction was performed in NMP
[7)] After in situ formation of the catalytic system (under vacuum at 60° C.), the reaction was performed at atmospheric pressure
[8)] The amino acid, the salt of the cation M and the starting diketone were reacted directly in DMSO at 60° C.
[9)] The reaction was performed with the conditions described by Agami et al, (see Bulletin de la Société Chimique de France, 1987, 358) but in DMF at room temperature
[10)] The reaction was performed using an amino acid which is not a primary one, but with the procedure of the present invention

Example 2

Preparation of Optical Active
15-Methylbicyclo[10.4.0]hexadec-1(12)-en-13-one

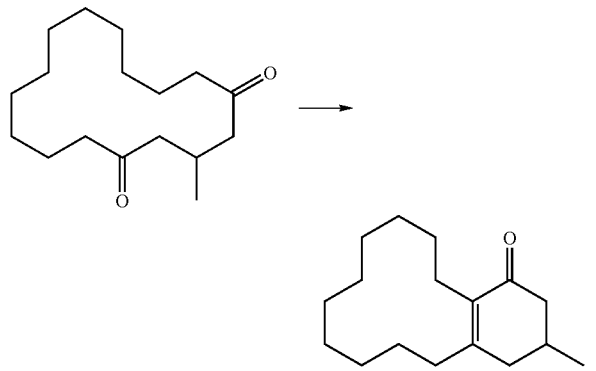

a) General Procedure:

In the reaction vessel, the catalytic system was formed in situ by stirring the optically active primary amino acid with an appropriate salt of the cation M or of the anion X, at 60° C. in 0.13 ml DMSO under vacuum (8 mbar) for 18 hours. After cooling down to 40° C., 50 mg of 3-methyl-1,5-cyclohexadecanedione were introduced in 0.1 ml of DMSO. The total amount of DMSO present was calculated in order to keep the concentration of the starting diketone between 0.1 and 1 M at the beginning of the reaction.

The reaction mixture was stirred under vacuum (8 mbar) at 40° C. and followed by GC. To stop the reaction, the mixture was hydrolyzed with water or an aqueous saturated $NH_4Cl$ solution. After extraction of the aqueous layer with diethyl ether, the organic layer was dried over $MgSO_4$ and filtered. The solvent was removed under vacuum and the residue was purified either by flash chromatography or by bulb to bulb distillation to yield in the desired product, i.e. (S)-15-methyl-bicyclo[10.4.0]hexadec-1(12)-en-13-one or (R)-15-methyl-bicyclo[10.4.0]hexadec-1(12)-en-13-one or an optically active mixture of said stereoisomers depending on the configuration of the amino acid.

$^1$H-NMR: 2.47-2.20 (m, 6H), 2.14-1.99 (m, 3H), 1.69-1.37 (m, 14H), 1.27-1.21 (m, 2H), 1.02 (d, J=5.1, 3H).

$^{13}$C-NMR: 199.8, 158.5, 135.1, 46.5, 38.9, 31.9, 29.8, 27.0, 26.3, 25.7, 25.5, 25.1, 24.2, 23.0, 22.8, 22.0, 21.2.

The results obtained are shown in Table 2.

TABLE 2 yields and e.e. of the final product as a function of the amino acid used

| | Catalytic system[a] | | | | |
|---|---|---|---|---|---|
| Amino acid[b] | Eq.[1] | Salt of the cation M or anion X | Eq.[1] | t[2] | Yield[3] | e.e[4] |
| D-Met | 1 | CsOH•$H_2O$ | 0.5 | 2 | 98% | 77% ee (S) |
| L-Phe* | 1 | Oxalic acid | 0.5 | 1 | 60% | 54% ee (R) |
| Se-L-Meth | 1 | CsOH•$H_2O$ | 0.5 | 10 | 93% | 62% ee (R) |
| D-Eth | 1 | CsOH•$H_2O$ | 0.5 | 8 | 84% | 56% ee (S) |
| D-Pyr-Ala | 1 | CsOH•$H_2O$ | 0.5 | 4 | 95% | 47% ee (R) |
| S-Eth-L-Cys | 1 | CsOH•$H_2O$ | 0.5 | 2 | 100% | 60% ee (R) |
| L-Phe** | 1 | pTsOH•$H_2O$ | 0.5 | 14 | 62% | 62% ee (R) |
| D-Meth | 1 | CsOH•$H_2O$ | 0.5 | 3 | 57% | 72% ee (S) |
| D-Meth | 1 | CsOH•$H_2O$ | 0.1 | 3 | 17% | 78% ee (S) |
| L-Trp | 1 | pTsOH•$H_2O$ | 0.5 | 7 | 75% | 57% ee (R) |

*the amino acid, the salt of the cation M or anion X and the starting diketone were reacted directly under vacuum in DMSO at 60° C.
**the amino acid, the salt of the cation M or anion X and the starting diketone were reacted directly under vacuum in DMSO at 40° C.
[a],[b],[1],[2],[3] and [4] are as explained in Example 1.

Example 3

Preparation of Optically Active
14-methyl-bicyclo[9.4.0]-pentadec-1(11)-en-12-one

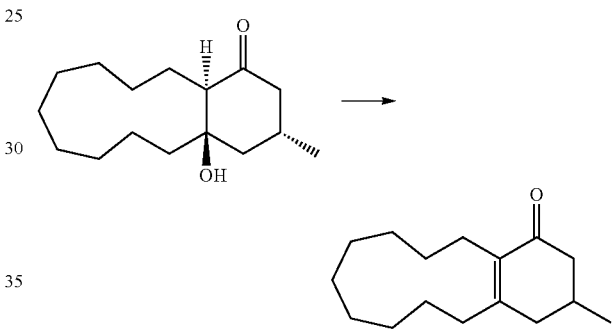

a) General Procedure:

In the reaction vessel, the catalytic system was formed in situ by stirring the optically active primary amino acid with an appropriate salt of the anion X, at 60° C. in 16 ml DMSO. Then 4 g of (11RS,14RS)-1-hydroxy-14-methyl-bicyclo [9.4.0]-pentadecan-12-one were introduced in 10 ml of DMSO. The total amount of DMSO present was calculated in order to keep the concentration of the starting ketone between 0.1 and 1 M at the beginning of the reaction.

The reaction mixture was stirred at 60° C. and followed by GC. To stop the reaction, the mixture was hydrolyzed with water or an aqueous saturated $NH_4Cl$ solution. After extraction of the aqueous layer with diethyl ether, the organic layer was dried over $MgSO_4$ and filtered. The solvent was removed under vacuum and the residue was purified either by flash chromatography or by bulb to bulb distillation to yield in the desired product, i.e. (S)-14-methyl-bicyclo[9.4.0]-pentadec-1(11)-en-12-one or (R)-14-methyl-bicyclo[9.4.0]-pentadec-1(11)-en-12-one or an optically active mixture of said stereoisomers depending on the configuration of the amino acid.

$^1$H-NMR: 1.04 (d, J=6.1, 3H), 1.18-1.46 (m, 10H), 1.50-1.75 (m, 4H), 1.97-2.15 (m, 3H), 2.30-2.40 (m, 3H), 2.41-2.56 (m, 3H).

$^{13}$C-NMR: 21.3, 23.5, 24.6, 25.1, 25.3, 25.5, 26.0, 26.2, 26.6, 29.7, 32.3, 38.3, 46.7, 136.3, 158.2, 199.7.

The results obtained are shown in Table 3.

TABLE 3 yields and e.e. of the final product as a function of the amino acid used

| | Catalytic system[a] | | | | |
|---|---|---|---|---|---|
| Amino acid[b] | Eq.[1] | Salt of the anion X | Eq.[1] | t[2] | Yield[3] | e.e[4] |
| pNO$_2$-L-Phe | 1 | pTsOH | 0.5 | 2.5 | 49% | 72% ee (S) |
| O—Me-L-Tyr | 1 | pTsOH | 0.5 | 1 | 39% | 80% ee (S) |
| L-Trp | 1 | pTsOH | 0.5 | 1 | 54% | 79% ee (S) |
| L-Homo-Ser | 1 | pTsOH | 0.5 | 1 | 47% | 63% ee (R) |
| S-Bz-L-Cys | 1 | pTsOH | 0.5 | 2 | 58% | 58% ee (S) |
| Se-L-Meth | 0.7 | pTsOH | 0.5 | 1 | 33% | 61% ee (S) |
| S-Prop-L-Cys | 0.5 | pTsOH | 0.5 | 2 | 44% | 46% ee (S) |
| L-Meth | 1 | pTsOH | 0.5 | 1 | 35% | 63% ee (S) |
| L-Ser | 1 | pTsOH | 0.5 | 2 | 40% | 56% ee (S) |
| D-Pyr-Ala | 1 | pTsOH | 0.5 | 5 | 58% | 54% ee (R) |
| S-Eth-L-Cys | 1 | pTsOH | 0.5 | 5 | 57% | 52% ee (S) |
| D-Eth | 1 | pTsOH | 0.5 | 5 | 55% | 56% ee (R) |
| L-Trp | 1 | pTsOH | 0.5 | 1 | 57% | 72% ee (S) |

[a],[b],[1],[2],[3] and [4] are as explained in Example 1

Example 4

Preparation of Optically Active 3-butyl-5-methyl-2-propyl-2-cyclohexen-1-one

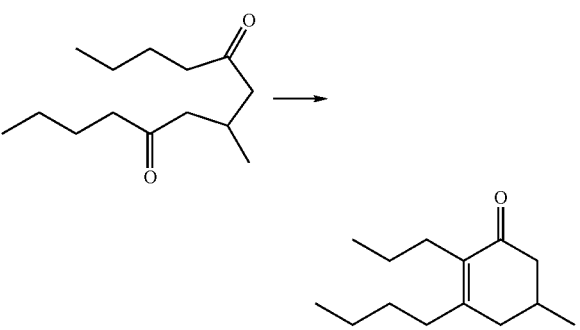

In the reaction vessel, the catalytic system was formed in situ by stirring the optically active primary amino acid with an appropriate salt of the anion X or cation M, in 0.3 ml DMSO. Then 50 mg of 7-methyl-5,9-tridecanedione were introduced in 0.3 ml of DMSO. The total amount of DMSO present was calculated in order to keep the concentration of the starting diketone between 0.1 and 1 mol/L at the beginning of the reaction.

The reaction mixture was stirred at 25° C. and followed by GC. To stop the reaction, the mixture was hydrolyzed with water or an aqueous saturated NH$_4$Cl solution. After extraction of the aqueous layer with diethyl ether, the organic layer was dried over MgSO$_4$ and filtered. The solvent was removed under vacuum and the residue was purified by flash chromatography to yield in the desired product, i.e. (S)-3-butyl-5-methyl-2-propyl-2-cyclohexen-1-one or (R)-3-butyl-5-methyl-2-propyl-2-cyclohexen-1-one, or an optically active mixture of said stereoisomers depending on the configuration of the amino acid.

$^1$H-NMR: 0.89 (t, J=7.7, 3H), 0.94 (t, J=7.2, 3H), 1.02 (d, J=6.2, 3H), 1.27-1.49 (m, 6H), 1.98-2.13 (m, 3H), 2.17-2.29 (m, 4H), 2.33 (d, J=15.3, 1H), 2.45 (d, J=14.4, 1H).

$^{13}$C-NMR: 14.0, 14.3, 21.2, 22.9, 23.0, 27.0, 29.8, 30.1, 34.7, 39.1, 46.2, 135.0, 158.3, 199.5.

The results obtained are shown in Table 4.

TABLE 4 yields and e.e. of the final product as a function of the amino acid used

| | Catalytic system[a] | | | | |
|---|---|---|---|---|---|
| Amino acid[b] | Eq.[1] | Salt of the cation M or anion X | Eq.[1] | t[2] | Yield[3] | e.e[4] |
| L-Pro[5] | 0.2 | — | — | 7 | 0 | — |
| L-Phe | 0.3 | CSA | 0.15 | 7 | 76% | 69% ee (R) |
| L-Phe | 0.3 | pTsOH•H$_2$O | 0.15 | 7 | 76% | 74% ee (R) |
| L-Phe | 0.3 | CF$_3$SO$_3$H | 0.15 | 7 | 77% | 72% ee (R) |
| L-Phe | 0.3 | (PhO)$_2$POOH | 0.15 | 7 | 91% | 70% ee (R) |
| L-Phe | 0.3 | H$_2$SO$_4$ | 0.15 | 7 | 77% | 72% ee (R) |
| L-Phe | 0.3 | CsF | 0.15 | 3 | 75% | 74% ee (R) |
| L-BnCys | 0.3 | CSA | 0.15 | 7 | 62% | 60% ee (R) |
| L-Tyr | 0.3 | CSA | 0.15 | 7 | 31% | 66% ee (R) |
| O—Me-L-Tyr | 0.3 | CSA | 0.15 | 7 | 74% | 69% ee (R) |
| L-Lys | 0.3 | CSA | 0.15 | 7 | 78% | 51% ee (R) |
| L-Trp | 0.3 | CSA | 0.15 | 7 | 84% | 77% ee (R) |
| L-Arg | 0.3 | CSA | 0.15 | 7 | 51% | 46% ee (R) |
| L-Met | 0.3 | CSA | 0.15 | 7 | 36% | 74% ee (R) |
| Se-L-Meth | 0.3 | CSA | 0.15 | 7 | 53% | 62% ee (R) |
| L-But-sulfox | 0.3 | CSA | 0.15 | 7 | 38% | 58% ee (R) |
| D-Eth | 0.3 | CSA | 0.15 | 7 | 64% | 64% ee (S) |
| D-Pyr-Ala | 0.3 | CSA | 0.15 | 7 | 80% | 66% ee (R) |
| L-Homo-Ser | 0.3 | CSA | 0.15 | 7 | 79% | 70% ee (R) |
| S-prop-L-Cys | 0.3 | CSA | 0.15 | 7 | 27% | 48% ee (R) |
| L-Trp | 0.3 | CsF | 0.3 | 3 | 75% | 75% ee (R) |
| D-Eth | 0.3 | CsF | 0.3 | 3 | 64% | 64% ee (S) |
| L-Trp | 0.3 | pTsOH•H2O | 0.15 | 7 | 76% | 73% ee (R) |
| L-Trp | 0.3 | CsF | 0.1 | 3 | 96% | 71% ee (R) |
| L-Trp | 0.3 | CsF | 0.5 | 3 | 53% | 58% ee (R) |
| L-Trp | 0.3 | — | | 3 | 80% | 62% ee (R) |
| S-Et-L-Cys | 0.5 | CsF | 0.3 | 7 | 86% | 57% ee (R) |
| S-Et-L-Cys | 0.5 | CSA | 0.3 | 7 | 63% | 51% ee (R) |
| D-Meth | 0.3 | CsF | 0.3 | 7 | 76% | 61% ee (S) |

[a],[b],[1],[2],[3] and [4] are as explained in Example 1
[5] The reaction was performed with the conditions described by Agami et al, (see Bulletin de la Société Chimique de France, 1987, 358) but in DMF at room temperature
CSA = campholenic sulfonic acid

Example 5

Preparation of Optical Active 13-methyl-bicyclo[8.4.0]tetradec-1(10)-en-11-one

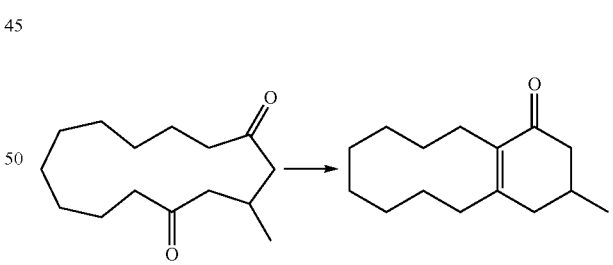

a) General Procedure:

In the reaction vessel, the catalytic system was formed in situ by stirring the optically active primary amino acid with an appropriate salt of the cation M or of the anion X, at 60° C. in 0.15 ml DMSO under vacuum (8 mbar) for 18 hours. Then 50 mg of 3-methyl-1,5-cyclotetradecanedione were introduced in 0.15 ml of DMSO. The total amount of DMSO present was calculated in order to keep the concentration of the starting diketone between 0.1 and 1 M at the beginning of the reaction.

The reaction mixture was stirred under vacuum (8 mbar) at 60° C. and followed by GC. To stop the reaction, the mixture was hydrolyzed with water or an aqueous saturated NH$_4$Cl solution. After extraction of the aqueous layer with diethyl ether, the organic layer was dried over MgSO$_4$ and filtered. The solvent was removed under vacuum and the residue was purified either by flash chromatography or by bulb to bulb distillation to yield in the desired product, i.e. (S)-13-methyl-bicyclo[8.4.0]tetradec-1(10)-en-11-one or (R)-13-methyl-bicyclo[8.4.0]tetradec-1(10)-en-11-one or an optically active mixture of said stereoisomers depending on the configuration of the amino acid.

$^1$H-NMR: 1.05 (d, J=6.2, 3H), 1.14-1.50 (m, 10H), 1.56-1.8 (m, 2H), 1.71-1.80 (m, 2H), 1.94-2.20 (m, 3H), 2.44-2.55 (m, 4H).

$^{13}$C-NMR: 21.1, 21.3, 21.4, 23.4, 25.5, 25.7, 25.8, 27.1, 29.7, 32.7, 38.0, 46.7, 134.8, 158.4, 199.5.

The results obtained are shown in Table 5.

TABLE 5 yields and e.e. of the final product as a function of the amino acid used

| Amino acid[b] | Catalytic system[a] | | | | |
|---|---|---|---|---|---|
| | Eq.[1] | Salt of the cation M or anion X | Eq.[1] | t[2] | Yield[3] | e.e[4] |
| D-Met | 1 | CsOH·H$_2$O | 0.5 | 3 | 95% | 90% ee (S) |
| L-Phe | 1 | Oxalic acid | 0.5 | 7 | 47% | 26% ee (R) |

[a],[b],[1],[2],[3] and [4] are as explained in Example 1

Example 6

Preparation of Optically Active 3-butyl-5-phenyl-2-propyl-2-cyclohexen-1-one

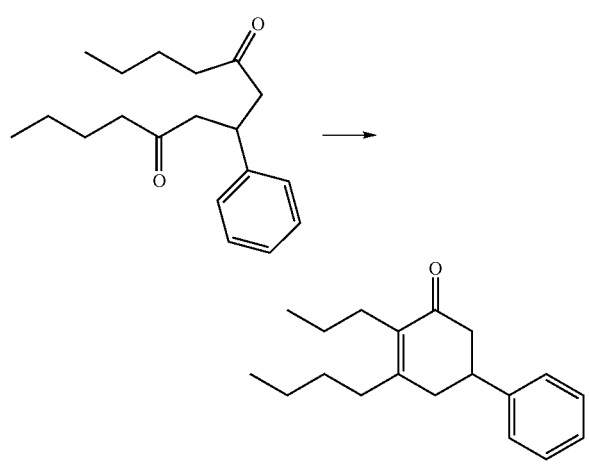

In the reaction vessel, the catalytic system was formed in situ by stirring the optically active primary amino acid with an appropriate salt of the anion X or cation M, in 0.3 ml DMSO. Then 50 mg of 7-phenyl-5,9-tridecanedione were introduced in 0.3 ml of DMSO. The total amount of DMSO present was calculated in order to keep the concentration of the starting diketone between 0.1 and 1 mol/L at the beginning of the reaction.

The reaction mixture was stirred at 25° C. and followed by GC. To stop the reaction, the mixture was hydrolyzed with water or an aqueous saturated NH$_4$Cl solution. After extraction of the aqueous layer with diethyl ether, the organic layer was dried over MgSO$_4$ and filtered. The solvent was removed under vacuum and the residue was purified by flash chromatography to yield in the desired product, i.e. (S)-3-butyl-5-phenyl-2-propyl-2-cyclohexen-1-one or (R)-3-butyl-5-phenyl-2-propyl-2-cyclohexen-1-one, or an optically active mixture of said stereoisomers depending on the configuration of the amino acid.

$^1$H-NMR: 0.93 (t, J=7.4, 6H), 1.33-1.55 (m, 6H), 2.24-2.36 (m, 4H), 2.52-2.74 (m, 4H), 3.18-3.27 (m, 1H), 7.22-7.27 (m, 3H), 7.31-7.36 (m, 2H).

$^{13}$C-NMR: 13.9, 14.3, 22.9, 23.0, 27.2, 27.4, 34.7, 38.7, 40.5, 44.7, 126.7, 126.8, 128.7, 135.3, 143.7, 158.1, 198.7.

The results obtained are shown in Table 6.

TABLE 6 yields and e.e. of the final product as a function of the amino acid used

| Amino acid[b] | Catalytic system[a] | | | | |
|---|---|---|---|---|---|
| | Eq.[1] | Salt of the cation M or anion X | Eq.[1] | t[2] | Yield[3] | e.e[4] |
| L-Trp | 0.3 | CSA | 0.15 | 7 | 92% | 81% (R) |
| L-Trp | 0.3 | CsF | 0.15 | 7 | 98% | 77% (R) |
| L-Phe | 0.3 | CSA | 0.15 | 14 | 84% | 81% ee (R) |
| L-Phe | 0.3 | CsF | 0.15 | 3 | 70% | 81% ee (R) |

[a],[b],[1],[2],[3] and [4] are as explained in Example 1.

Example 7

Preparation of Optically Active 2-ethyl-5-methyl-3-propyl-2-cyclohexen-1-one

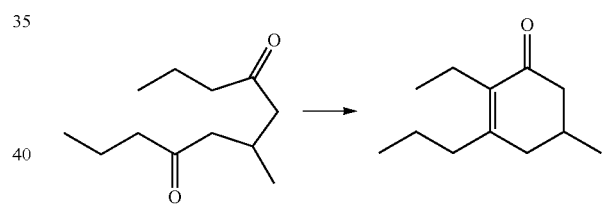

In the reaction vessel, the catalytic system was formed in situ by stirring the optically active primary amino acid with an appropriate salt of the anion X or cation M, in 0.3 ml DMSO. Then 50 mg of 6-methyl-4,8-undecanedione were introduced in 0.3 ml of DMSO. The total amount of DMSO present was calculated in order to keep the concentration of the starting diketone between 0.1 and 1 mol/L at the beginning of the reaction.

The reaction mixture was stirred at 25° C. and followed by GC. To stop the reaction, the mixture was hydrolyzed with water or an aqueous saturated NH$_4$Cl solution. After extraction of the aqueous layer with diethyl ether, the organic layer was dried over MgSO$_4$ and filtered. The solvent was removed under vacuum and the residue was purified by flash chromatography to yield in the desired product, i.e. (S)-2-ethyl-5-methyl-3-propyl-2-cyclohexen-1-one or (R)-2-ethyl-5-methyl-3-propyl-2-cyclohexen-1-one, or an optically active mixture of said stereoisomers depending on the configuration of the amino acid.

$^1$H-NMR: 0.92 (t, J=7.8, 3H), 0.97 (t, J=7.2, 3H), 1.03 (d, J=5.9, 3H), 1.45-1.58 (m, 2H), 1.98-2.13 (m, 3H), 2.20-2.37 (m, 5H), 2.45 (d, J=14.4, 1H).

$^{13}$C-NMR: 14.1, 14.3, 18.3, 21.2, 29.8, 36.7, 39.0, 46.2, 136.6, 157.6, 199.3.

The results obtained are shown in Table 7.

TABLE 7 yields and e.e. of the final product as a function of the amino acid used

| Catalytic system[a]| | | | | |
|---|---|---|---|---|---|
| Amino acid[b] | Eq.[1] | Salt of the cation M or anion X | Eq.[1] | t[2] | Yield[3] | e.e[4] |
| L-Trp | 0.3 | CSA | 0.15 | 7 | 96% | 59% ee (R) |
| L-Trp | 0.3 | CsF | 0.15 | 7 | 89% | 44% ee (R) |
| L-Phe | 0.3 | — | | 15 | 12% | 69% ee (R) |
| L-Phe | 0.3 | CSA | 0.15 | 7 | 80% | 68% ee (R) |

[a),b),1),2),3)] and [4)] are as explained in Example 1.

Example 8

Preparation of Optically Active (−)-(3S,9Z)-3-methyl-2,3,4,5,6,7,8,11,12,13-decahydro-1H-benzocycloundecen-1-one

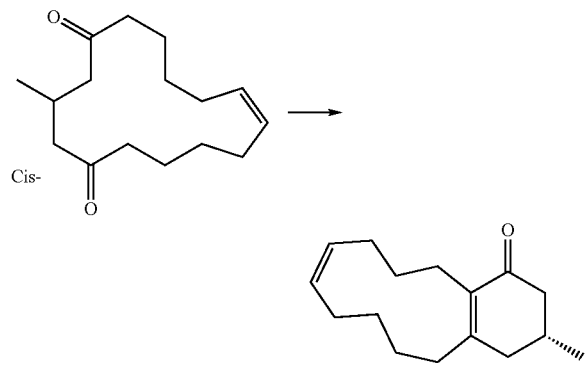

a) General Procedure:

In the reaction vessel, the amino acid, the salt of the cation M or anion X and the starting diketone (10Z)-3-methyl-10-cyclopentadecene-1,5-dione were reacted directly under vacuum in 0.5 ml of DMSO at 60° C.

The reaction mixture was stirred under vacuum (8 mbar) at 60° C. and followed by GC. To stop the reaction, the mixture was hydrolyzed with water or an aqueous saturated $NH_4Cl$ solution. After extraction of the aqueous layer with diethyl ether, the organic layer was to dried over $MgSO_4$ and filtered. The solvent was removed under vacuum and the residue was purified either by flash chromatography or by bulb to bulb distillation to yield in the desired product, i.e. cis-(S)-3-methyl-2,3,4,5,6,7,8,11,12,13-decahydro-1H-benzocycloundecen-1-one or an optically active mixture of said stereoisomers depending on the configuration of the amino acid.

Cis-:

$^{13}C$-NMR: 21.3, 22.9, 24.9, 26.3, 27.8, 29.6, 29.8, 30.3, 32.8, 38.1, 46.5, 131.7, 132.5, 160.5, 199.9.

The results obtained are shown in Table 8.

TABLE 8 yields and e.e. of the final product as a function of the catalytic system used

| Catalytic system[a]| | | | | |
|---|---|---|---|---|---|
| Amino acid[b] | Eq.[1] | Salt of the cation M or anion X | Eq.[1] | t[2] | Yield[3] | e.e[4] |
| D-Met | 1 | CsOH•$H_2O$ | 0.5 | 1 | 95% | 44% ee (S) |

[a),b),1),2),3)] and [4)] are as explained in Example 1.

Example 9

Preparation of Optically Active (3R or 3S,9E)-3-methyl-2,3,4,5,6,7,8,11,12,13-decahydro-1H-benzocycloundecen-1-one

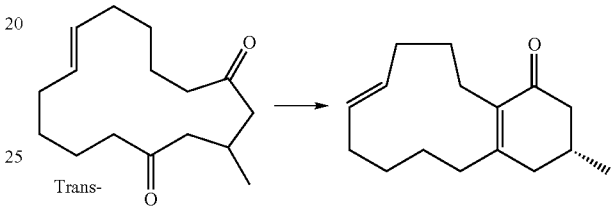

a) General Procedure:

In the reaction vessel, the amino acid, the salt of the cation M or anion X and the starting diketone (10E)-3-methyl-10-cyclopentadecene-1,5-dione were reacted directly under vacuum in 0.5 ml of DMSO at 60° C.

The reaction mixture was stirred under vacuum (8 mbar) at 60° C. and followed by GC. To stop the reaction, the mixture was hydrolyzed with water or an aqueous saturated $NH_4Cl$ solution. After extraction of the aqueous layer with diethyl ether, the organic layer was dried over $MgSO_4$ and filtered. The solvent was removed under vacuum and the residue was purified either by flash chromatography or by bulb to bulb distillation to yield in the desired product, i.e. trans-(S)-3-methyl-2,3,4,5,6,7,8,11,12,13-decahydro-1H-benzocycloundecen-1-one or trans-(R)-3-methyl-2,3,4,5,6,7,8,11,12,13-decahydro-1H-benzocycloundecen-1-one or an optically active mixture of said stereoisomers depending on the configuration of the amino acid.

Trans-:

$^1H$-NMR: 1.01 (d, J=6.1, 3H), 1.20-1.34 (m, 4H), 1.42-1.70 (m, 6H), 1.93-2.20 (m, 7H), 2.22-2.36 (m, 2H), 2.40-2.54 (m, 2H).

$^{13}C$-NMR: 21.3, 23.8, 26.0, 26.8, 28.3, 29.8, 33.4, 33.7, 34.3, 38.1, 46.5, 130.9, 132.3, 135.8, 156.6, 200.4.

The results obtained are shown in Table 9.

TABLE 9 yields and e.e. of the final product as a function of the catalytic system used

| Catalytic system[a]| | | | | |
|---|---|---|---|---|---|
| Amino acid[b] | Eq.[1] | Salt of the cation M or anion X | Eq.[1] | t[2] | Yield[3] | e.e[4] |
| D-Phe | 1 | Oxalic acid | 0.5 | 4 | 97% | 73% ee (S) |
| D-Meth | 1 | CsOH•$H_2O$ | 0.5 | 2 | 100% | 80% ee (S) |
| L-Phe | 1 | CSA | 0.5 | 30 | 15% | 89% ee (R) |

[a),b),1),2),3)] and [4)] are as explained in Example 1.

Example 10

Preparation of Optically Active 3-(hex-5-enyl)-5-methyl-2-(pent-4-enyl)-2-cyclohexen-1-one

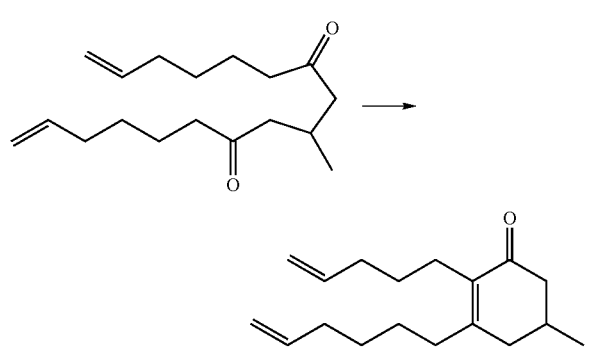

In the reaction vessel, the catalytic system was formed in situ by stirring the optically active primary amino acid with an appropriate salt of the anion X, in 0.3 ml DMSO. Then 50 mg of 9-methyl-1,16-heptadecadiene-7,11-dione were introduced in 0.3 ml of DMSO. The total amount of DMSO present was calculated in order to keep the concentration of the starting diketone between 0.1 and 1 mol/L at the beginning of the reaction.

The reaction mixture was stirred at 25° C. and followed by GC. To stop the reaction, the mixture was hydrolyzed with water or an aqueous saturated $NH_4Cl$ solution. After extraction of the aqueous layer with diethyl ether, the organic layer was dried over $MgSO_4$ and filtered. The solvent was removed under vacuum and the residue was purified by flash chromatography to yield in the desired product, i.e. (S)-3-(hex-5-enyl)-5-methyl-2-(pent-4-enyl)-2-cyclohexen-1-one or (R)-3-(hex-5-enyl)-5-methyl-2-(pent-4-enyl)-2-cyclohexen-1-one or an optically active mixture of said stereoisomers depending on the configuration of the amino acid.

$^1$H-NMR: 1.02 (d, J=6.1, 3H), 1.33-1.52 (m, 6H), 1.97-2.14 (m, 6H), 2.19-2.40 (m, 5H), 2.42-2.50 (m, 2H), 4.90-5.08 (m, 4H), 5.73-5.89 (m, 2H).

$^{13}$C-NMR: 21.2, 24.6, 27.3, 28.8, 29.0, 29.8, 33.5, 34.0, 34.7, 39.1, 46.2, 114.4, 114.8, 135.0, 138.4, 138.8, 158.1, 199.4.

The results obtained are shown in Table 10.

TABLE 10 yields and e.e. of the final product as a function of the amino acid used

| Catalytic system[a] | | | | | |
|---|---|---|---|---|---|
| Amino acid[b] | Eq.[1] | Salt of the cation M or anion X | Eq.[1] | t[2] | Yield[3] | e.e[4] |
| L-Phe | 0.3 | CSA | 0.15 | 7 | 67% | 77% ee (R) |
| D-Phe | 0.3 | CSA | 0.15 | 7 | 83% | 71% ee (S) |

[a),b),1),2),3)] and [4)] are as explained in Example 1.

Example 11

Preparation of Optically Active 13-methyl-bicyclo[8.4.0]tetradec-1(10)-en-11-one

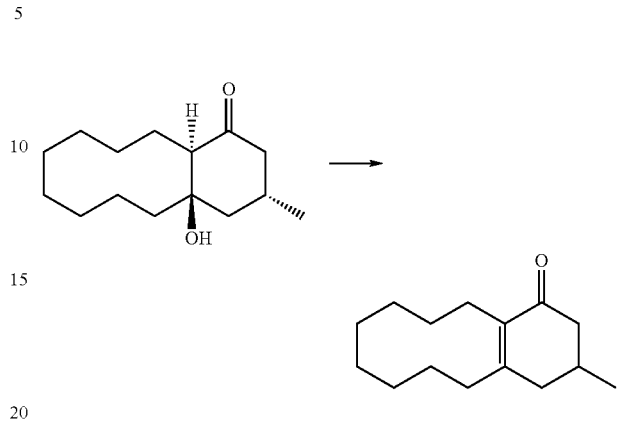

a) General Procedure:

In the reaction vessel, the catalytic system was formed in situ by stirring the optically active primary amino acid with an appropriate salt of the anion X, at 60° C. in 0.2 ml DMSO. Then 50 mg of (10RS,13RS)-1-hydroxy-13-methyl-bicyclo[8.4.0]tetradecan-11-one were introduced. The total amount of DMSO present was calculated in order to keep the concentration of the starting ketone between 0.1 and 1 M at the beginning of the reaction.

The reaction mixture was stirred at 60° C. and followed by GC. To stop the reaction, the mixture was hydrolyzed with water or an aqueous saturated $NH_4Cl$ solution. After extraction of the aqueous layer with diethyl ether, the organic layer was dried over $MgSO_4$ and filtered. The solvent was removed under vacuum and the residue was purified either by flash chromatography or by bulb to bulb distillation to yield in the desired product.

$^1$H-NMR: 1.05 (d, J=6.2, 3H), 1.14-1.50 (m, 10H), 1.56-1.8 (m, 2H), 1.71-1.80 (m, 2H), 1.94-2.20 (m, 3H), 2.44-2.55 (m, 4H).

$^{13}$C-NMR: 21.1, 21.3, 21.4, 23.4, 25.5, 25.7, 25.8, 27.1, 29.7, 32.7, 38.0, 46.7, 134.8, 158.4, 199.5.

The results obtained are shown in Table 11.

TABLE 11 yields and e.e. of the final product as a function of the amino acid used

| Catalytic system[a] | | | | | |
|---|---|---|---|---|---|
| Amino acid[b] | Eq.[1] | Salt of the anion X | Eq.[1] | t[2] | Yield[3] | e.e[4] |
| o-Met-L-Tyr | 1 | pTsOH | 0.5 | 1 | 20% | 55% ee (R) |

[a),b),1),2),3)] and [4)] are as explained in Example 1.

What is claimed is:
1. A process for the preparation of a compound of formula

(I)

wherein:
the asterisk indicates that the compound (I) is in an optically active form;
the $R^1$, taken separately, are identical and represent an achiral $C_{1-7}$ linear, branched or cyclic alkyl, alkenyl or alkynyl group optionally substituted, or alternatively two $R^1$, taken together, represent a linear $C_2$-$C_{12}$ alkanediyl, alkenediyl or alkyndiyl group optionally substituted;
$R^2$ represents an achiral $C_{1-7}$ linear, branched or cyclic alkyl or alkenyl group optionally substituted or a phenyl or benzyl group optionally substituted;
by treating a ketone of one of formulae:

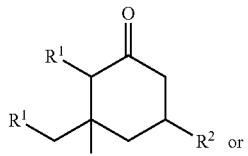

(II)

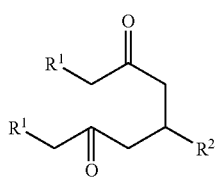

(III)

wherein compound (II) can be in the form of any one of its stereoisomers, diastereoisomers or of a mixture thereof,
with a reacting system comprising:
at least one salt of an optically active primary amino acid, or
at least one optically active primary amino acid, or
a mixture thereof
under conditions sufficient to form the compound of formula (I).

2. The process according to claim 1, wherein the compound (I) is (S)-14-methyl-bicyclo[9.4.0]pentadec-1(11)-en-12-one or (R)-14-methyl-bicyclo[9.4.0]pentadec-1(11)-en-12-one or an optically active mixture of the stereoisomers and the starting ketone is 3-methyl-1,5-cyclopentadecanedione, or the compound (I) is 15-methylbicyclo[10.4.0]hexadec-1(12)-en-13-one and the starting ketone is 3-methyl-1,5-cyclohexadecanedione, or the compound (I) is (R)-13-methylbicyclo[8.4.0]tetradec-1(10)-en-11-one or (S)-13-methylbicyclo[8.4.0]tetradec-1(10)-en-11-one or an optically active mixture of the stereoisomers and the starting ketone is 3-methyl-1,5-cyclotetradecanedione, or the compound (I) is (R)-15-methylbicyclo[10.4.0]hexadec-1(12)-en-13-one or (S)-15-methylbicyclo[10.4.0]hexadec-1(12)-en-13-one or an optically active mixture of the stereoisomers and the starting ketone is 3-methyl-1,5-cyclohexadecanedione.

3. The process according to claim 1, wherein the salt of an optically active primary amino acid is a compound of formula (III)

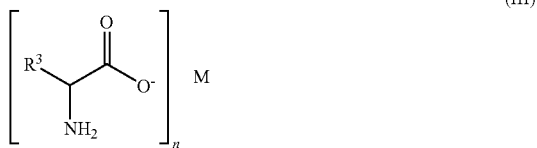

wherein $R^3$ represents $C_6$-$C_{11}$ hydrocarbon group comprising 3 to 7 nitrogen or oxygen atoms or a $C_1$-$C_{16}$ hydrocarbon group optionally comprising from one to four heteroatoms of oxygen, nitrogen, sulfur, phosphorous, halogen or selenium; and
M represents
an alkaline cation or a $C_4$-$C_{15}$ quaternary ammonium, and n is 1;
an alkaline-earth cation, and n is 2; or
a lanthanide or a Group (III) cation, and n is 3.

4. The process according to claim 3, wherein the $R^3$ group represents:
a linear, branched or cyclic $C_3$-$C_7$ alkyl group;
a $(CH_2)_c R^4$ group wherein c is 1 or 2, and $R^4$ represents a COOH or $CONH_2$;
a $CH_2 R^6$ group, $R^6$ an $C_3H_3N_2$ or a $C_8H_6N$ heterocyclic group;
a $CH_2(CH_2)_c R^7$, $R^7$ being a $NHC(NH)NH_2$, a $CH_2NH_2$ group, c is 1 or 2;
a $(CH_2)_c C_6H_{5-v} R^{5'}_v$ group, wherein $R^{5'}$ represents a $R^5$ group, nitro group or a $OR^5$ group, v is 0, 1 or 2, $R^5$ representing a hydrogen atom or a methyl or benzyl group, and c is 1 or 2;
a $(CH_2)_2S(O)_2R^9$ or a $(CH_2)_2S(O)(NH)R^9$, wherein $R^9$ represents a $C_1$-$C_5$ alkyl group; or
a $(CH_2)_c SR^8$ group, wherein $R^8$ represents a hydrogen atom, a methyl group, or a $CH_2(C_6H_{5-v}R^{5'}_v)$ group, wherein v is 0, 1 or 2, c is 1 or 2, and $R^{5'}$ represents a $R^5$ group, nitro group or a $OR^5$ group, v is 0, 1 or 2, $R^5$ representing a hydrogen atom or a methyl or benzyl group.

5. The process according to claim 3, wherein the M is an alkaline cation, $Ba^{2+}$, a $C_6$-$C_{10}$ quaternary ammonium, $La^{3+}$.

6. The process according to claim 1, wherein the salt of an optically active primary amino acid is a compound of formula (IV)

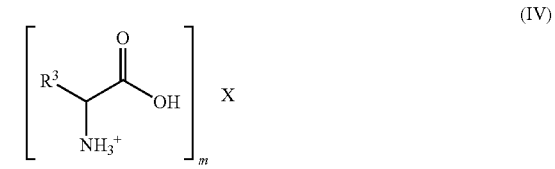

wherein $R^3$ has the same meaning as in formula (III) and
X represents
nitrate, hydrogeno sulfate, hydrogeno carbonate, a halide, a $C_0$-$C_{18}$ sulfonate, $C_0$-$C_{24}$ borate, a $C_2$-$C_{18}$ phosphonate or phosphate or phosphinate, or a $C_1$-$C_{12}$ mono carboxylate, and m is 1; or
sulfate, carbonate or a $C_2$-$C_{12}$ di-carboxylate, and m is 2, or an anion of formula $H_vPO_3^{(3-v)-}$, v being 0, 1 or 2, and m is 1, 2 or 3.

7. The process according to claim 6, wherein X is $CF_3SO_3^-$, $nC_{18}H_{30}SO_3^-$, $HSO_4^-CH_3CO_2^-$, $ClCH_2CO_2^-$, camphor sulfonate, $C_6H_5SO_3^-$, $MeC_6H_5SO_3^-$, $BF_4^-$, $(C_6H_5O)_2P(O)O^-$, $(BuO)_2P(O)O^-$, $(C_6H_5)_2P(O)O^-$, $(tBu)P(OH)_2O^-$, $(C_6H_5)P(OH)_2O^-$, a $C_1$-$C_3$ alkyl carboxylate, $CF_3COO^-$, $(CF_3SO_3)_2N^-$, oxalate or phthalate.

8. The process according to claim 1, wherein the reacting system comprises:
at least one salt of an optically active primary amino acid; and
optionally at least one optically active primary amino acid.

9. The process according to claim 8, wherein the optically active primary amino acid is added to the reaction medium in a total concentration ranging from 00.1 and 10 molar equivalents, relative to the optically active primary amino acid salt total concentration.

10. The process according to claim 1, wherein the optically active primary amino acid salt is formed in situ by reacting at least one optically active primary amino acid with an appropriate salt of cation M or anion X.

11. The process according to claim 1, performed while water is removed.

12. The process according to claim 11, wherein the water is removed by adsorption, normal distillation, azeotropic distillation or chemically by contact with:

an alkaline or alkaline earth hydride;

a reaction-medium insoluble inorganic material capable to form a clathrate with water; or an organic material capable of reacting with water to form non-acidic compounds.

13. The process according to claim 11, wherein the water is removed by contact with NaH, KH, $CaH_2$, LiH, or $MgH_2$.

14. The process according to claim 11, wherein the water is removed by contact with an anhydrous zeolite of the 4 or 5 Å type, or anhydrous $MgSO_4$, $Na_2SO_4$, $Na_2O$, $CaCl_2$ or $MgCl_2$.

15. The process according to claim 11, wherein the water is removed by contact with an orthoester, N-methyl-N-trimethylsilyl-trifluoroacetamide or 1-trimethyl-silylimidazole.

* * * * *

UNITED STATES PATENT AND TRADEMARK OFFICE
CERTIFICATE OF CORRECTION

PATENT NO.       : 8,173,846 B2
APPLICATION NO.  : 12/810735
DATED            : May 8, 2012
INVENTOR(S)      : Knopff It is certified that error appears in the above-identified patent and that said Letters Patent is hereby corrected as shown below:

<u>Column 22:</u>
Line 55 (claim 7, line 2), "$HSO_4^- CH_3CO_2^-$," to -- $HSO_4^-$, $CH_3CO_2^-$, --.

Signed and Sealed this
Nineteenth Day of June, 2012

David J. Kappos
*Director of the United States Patent and Trademark Office*